United States Patent [19]

Monguzzi et al.

[11] 4,124,594
[45] Nov. 7, 1978

[54] 4-HYDROXY PYRROLIDIN-2-ONYL-AMIDES

[75] Inventors: Riccardo Monguzzi, Corsico (Milan); Giorgio Pifferi, Milan, both of Italy

[73] Assignee: I.S.F. Spa, Milan, Italy

[21] Appl. No.: 876,167

[22] Filed: Feb. 8, 1978

[30] Foreign Application Priority Data

Feb. 11, 1977 [IT] Italy .................. 20226 A/77

[51] Int. Cl.$^2$ .......................................... C07D 207/28
[52] U.S. Cl. .............................. 260/326.43; 424/274
[58] Field of Search ................... 260/326.43

[56] References Cited

FOREIGN PATENT DOCUMENTS 2,635,853  2/1977  Fed. Rep. of Germany.
2,635,854  2/1977  Fed. Rep. of Germany.

OTHER PUBLICATIONS

Aatnaa, E. et al., "J. Int. Med. Res.," (1975) 3, pp. 352–356.

Primary Examiner—Donald G. Daus
Assistant Examiner—Lisa Jones
Attorney, Agent, or Firm—Stevens, Davis, Miller & Mosher

[57] ABSTRACT

Pyrrolidine derivatives of the formula

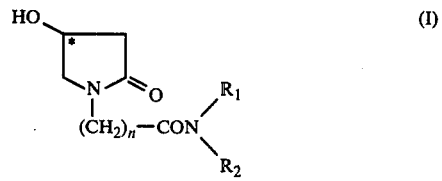

are prepared from γ-amino-β-hydroxybutyric acid which, after reaction with a silylating agent, is reacted, in the presence of an acid acceptor, with a halogen derivative of an ester of an aliphatic acid and then cyclized to give the corresponding N-alkoxy-carbonylalkyl derivative which is converted into the corresponding amide by treatment with ammonia or with a mono- or di-substituted amine. The compounds produced by the present invention improve learning memory and display a protecting effect against the E.E.G. consequence of an overdose of barbituates and against the reduced performance following brain damage (e.g. cerebral edema).

7 Claims, No Drawings

4-HYDROXY PYRROLIDIN-2-ONYL-AMIDES

The present invention concerns a new process for the preparation of pyrrolidine derivatives.

The pyrrolidine derivatives with which the present invention is concerned are compounds of the general formula:

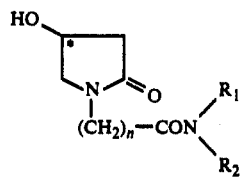

wherein $n$ is 1, 2 or 3, $R_1$ and $R_2$, which can be the same or different, are hydrogen or alkyl containing 1 to 3 carbon atoms and the asterisk indicates the center of asymmetry of the molecule.

The compounds (I), whether in the racemic or optically-active form, display activity on the central nervous system and fall within a wider class of compounds described and claimed in our U.S. patent application Ser. No. 713,901 filed Aug. 12, 1976.

The method therein described for the preparation of such compounds comprises several steps starting from compounds, the preparation of which is complex. According to the present invention, there is provided a process which, in comparison with the process known from our above-mentioned application, enables one to obtain the desired compounds in a smaller number of steps, using simple and convenient starting materials.

Thus, according to the process of the present invention, compounds of general formula (I) are prepared from γ-amino-β-hydroxybutyric acid which, after reaction with a silylating agent, is reacted, in the presence of an appropriate acid acceptor, with a halogen derivative of an appropriate ester of an appropriate aliphatic acid and then cyclized to give the corresponding N-alkoxycarbonylalkyl derivative which is inverted into the corresponding amide by treatment with ammonia or with an appropriate mono- or di-substituted amine. The process can be schematically represented as follows:

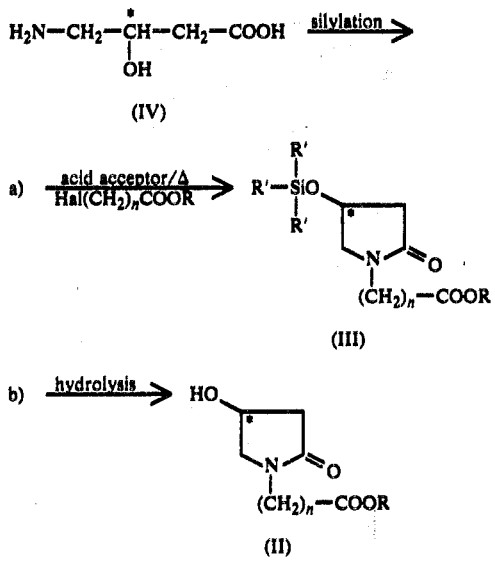

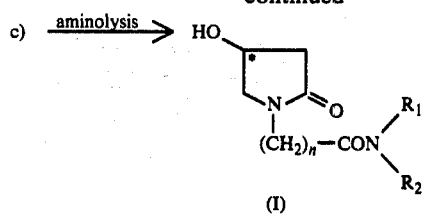

In the above general formulae, R' is methyl or ethyl, Hal is bromine, chlorine or iodine, R is alkyl containing 1 to 4 carbon atoms or trichlorophenyl, nitrophenyl or trichloroethyl, the asterisk indicates the center of asymmetry of the molecule and $n$ is 1, 2 or 3. Steps a) and b) of the above process can be carried out without separating the intermediate compound (III) and good yields are obtained.

As an acceptor for the hydrohalic acid formed in step a), there can be used basic ion-exchange resins, for example IRA 68, or olefin oxides, for example propylene oxide, or magnesium and calcium oxides.

The silylating agent used can be, for example, hexamethyldisilazane, bis-(trimethylsilyl)-urea or bis-(trimethylsilyl)-acetamide: in practice, it is preferred to use the selected silylating agent in the presence of a small quantity of trimethylchlorosilane.

According to the process of the present invention, γ-amino-β-hydroxybutyric acid (IV) can be used in enantiomeric form or in the form of a mixture. It is reacted under anhydrous conditions in a low boiling, inert, aprotic solvent or preferably in a mixture of such solvents, such as a mixture of acetonitrile with methylene chloride or chloroform, with an excess of silylating agent at the boiling temperature of the solvent used. The silyl derivative formed is reacted, in the presence of an appropriate acid acceptor, with the halogen derivative of an ester of an aliphatic acid of the general formula Hal(CH$_2$)$_n$—COOR, wherein Hal, $n$ and R have the same meanings as above. The reaction mixture is warmed up to a temperature of from 30° to 80° C. The silyl derivative (III) can be hydrolyzed to give the corresponding O-hydroxy derivative (II) from which, by reaction with concentrated ammonia or with a mono- or disubstituted amine of the general formula NHR$_1$R$_2$, where R$_1$ and R$_2$ have the same meanings as above, except that both cannot be hydrogen atoms, the desired compound (I) is obtained. In order to obtain unsubstituted amides, the silyl derivative (III) can be directly reacted with ammonia in solution without previous hydrolysis.

Compounds (I) and (II) can be acylated in a known manner to give the corresponding O-acyl derivatives. Particularly preferred are the derivatives with acetic, propionic, butyric, valeric, hexanoic, malonic, succinic, benzoic and the like acids.

The following Examples are given for the purpose of illustrating the present invention:

EXAMPLE 1

2-(4-Hydroxypyrrolidin-2-on-1-yl)-ethyl acetate

Twenty-eight ml. of hexamethyldisilazane and 3 drops of trimethylchlorosilane are added to 10 g. γ-amino-3-hydroxybutyric acid in 100 ml. anhydrous acetonitrile. The reaction mixture is heated under reflux in a current of nitrogen until a clear solution is obtained. The resulting mixture is cooled to ambient temperature and 50 ml. propylene oxide are added thereto, followed by the dropwise addition of 9.4 ml. ethyl bromoacetate. The reaction mixture is heated under reflux for 15 hours, cooled to ambient temperature and then evaporated to dryness in vacuo. The residue obtained, which contains crude 2-(4-trimethyl-silyloxypyrrolidin-2-on-1-yl)-ethyl acetate is separated by chromatography on a eluting silica gel column, using ethyl acetate as elution agent. Eight g. 2-(4-Hydroxypyrrolidin-2-on-1-yl)-ethyl acetate are obtained in the form of a colorless oil; b.p. 180° C./0.8 mm.Hg.

EXAMPLE 2

2-(4-Hydroxypyrrolidin-2-on-1-yl)-acetamide

A solution of 7.1 g. 2-(4-hydroxypyrrolidin-2-on-1-yl)-ethyl acetate (obtained as described in Example 1) in 7.1 ml. ammonium hydroxide solution ($d_{25}0.90$) is stirred at ambient temperature for 15 hours. The reaction mixture is then diluted with 40 ml. acetone and stirring is continued at ambient temperature until the gummy precipitate formed solidifies into white crystals. By suction filtration and drying, there are obtained 5.1 g. 2-(4-hydroxypyrrolidin-2-on-1-yl)-acetamide; m.p. 160°–162° C.; Rf 0.32 on silica gel (eluant: acetonitrile/water 4:1 v/v).

EXAMPLE 3

R(+)-2-(4-hydroxypyrrolidin-2-on-1-yl)-acetamide

The procedure is as described above, using, as the starting material, R(−)-γ-amino-β-hydroxybutyric acid and preparing successively R(+)-2-(4-hydroxypyrrolidin-2-on-1-yl)-ethyl acetate (b.p. 179° C./0.8 mm. Hg) and then R(+)-2-(4-hydroxypyrrolidin-2-on-1-yl)-acetamide (m.p. 135°–136° C.; $[\alpha]_D^{25} = +36.2°$ (water, $c = 1$)).

EXAMPLE 4

3-(4-Hydroxypyrrolidin-2-on-1-yl)-propionamide

Proceeding as described above and using ethyl 3-bromopropionate instead of ethyl bromoacetate, there is first obtained 3-(4-hydroxypyrrolidin-2-on-1-yl)-ethyl propionate (b.p. 190° C./0.8 mm. Hg, with decomposition) and then 3-(4-hydroxypyrrolidin-2-on-1-yl)-propionamide (m.p. 99°–100° C.).

EXAMPLE 5

2-(4-Acetoxypyrrolidin-2-on-1-yl)-ethyl acetate

To a solution of 2 g. of 2-(4-hydroxypyrrolidin-2-on-1-yl)-ethyl acetate (prepared as described in Example 1) in 20 ml. anhydrous pyridine is added 0.9 ml. acetyl chloride. The reaction mixture is stirred overnight at ambient temperature and then poured into 50 ml. water containing 14 ml. concentrated sulphuric acid. The resulting mixture is extracted with ethyl acetate and the organic phases are collected, washed with a saturated aqueous ammonium sulphate solution, dried and evaporated to dryness. The residue is chromatographed on silica gel, using diethyl ether as the elution agent, to give 2 g. 2-(4-acetoxy-pyrrolidin-2-on-1-yl)-ethyl acetate; b.p. 158° C./0.1 mm. Hg; Rf = 0.36 silica gel (eluant: ethyl acetate).

EXAMPLE 6

N-Ethyl-2-(4-hydroxypyrrolidin-2-on-1-yl)-acetamide

Proceeding as described in Example 1 but, instead of ethyl bromoacetate, using trichlorophenyl bromoacetate, there is obtained 2-(4-hydroxypyrrolidin-2-on-1-yl)-trichlorophenyl acetate.

Five g. 2-(4-Hydroxypyrrolidin-2-on-1-yl)-trichlorophenyl acetate are dissolved in 100 ml. methanol, the solution is cooled to 0° C. and 10 ml. ethylamine are added thereto. The reaction mixture is left to stand for 48 hours at ambient temperature, evaporated to dryness and subjected to chromatography to give 0.4 g. N-ethyl-2-(4-hydroxypyrrolidin-2-on-1-yl)-acetamide; m.p. 84°–86° C.; Rf = 0.23 silica gel (eluant: ethyl acetate).

The compounds produced by the process of the present invention are known to display learning memory activity which has been studied mostly utilizing as a comparison compound, Piracetam, the most closely related compound both as to chemical structure and pharmacological behavior. The compounds were studied according to the method described in J. Pharmacol. (Paris) 1972, 3, 1, pages 17–30, in which the animals to be treated were placed at the entrance of a maze filled with cold water (15° C.) at a depth of 24 cm and required to find the exit. A lamp placed at the entrance of the maze helped the animals in getting the right direction. Inside the maze there are a number of compartments which the animals should avoid. The exit is formed by a metal rectangular grate inclined at 45° resting on the bottom.

Male Wistar rats weighing 160–170 g. were used. The animals were placed at the entrance, and once they reached the exit, they ran up the inclined grate to get out of the water. Once out of the maze they were kept 1 hour in the warmth under an infrared lamp to let them dry, and then put into their cage until the next successive passage in the maze. The compounds to be studied as well as simple saline solutions and the reference compound were administered half an hour before and 1 hour after each of the two daily trials, that is at 10:00 a.m. and 4:00 p.m. The number of errors and time spent to reach the exit were evaluated and demonstrated that the rats treated with the compounds of the invention learned significantly quicker than the animals treated with the saline solution and with the standard compound.

In the following table the average values ± S.E. obtained in each training session for the compound produced by the invention are given.

TABLE

| No. animals | TREATMENT | Dose mg/kg and route | Number of errors ± S.E. | | | | |
|---|---|---|---|---|---|---|---|
| | | | Session 1 | Session 2 | Session 3 | Session 4 | Session 5 |
| 40 | Saline | | 18.8 ± 1.2 | 11.6 ± 1.1 | 7.4 ± 0.9 | 5.6 ± 0.9 | 3.4 ± 0.4 |
| 15 | 2-(4-Hydroxy-pyrrolidin-2-on-1-yl)-acetamide | 10 i.p. | 16.5 ± 3.0 | 8.7 ± 1.5 | *3.3 ± 1.0 | *2.7 ± 1.1 | *1.8 ± 0.3 |
| 15 | 2-(4-Hydroxy-pyrrolidin-2-on-1-yl)-acetamide | 10 os | 17.0 ± 2.0 | 8.7 ± 1.6 | *4.6 ± 1.0 | *2.2 ± 0.5 | 2.0 ± 0.4 |

TABLE-continued

| No. animals | TREATMENT | Dose mg/kg and route | Number of errors ± S.E. | | | | |
|---|---|---|---|---|---|---|---|
| | | | Session 1 | Session 2 | Session 3 | Session 4 | Session 5 |
| 15 | piracetam | 30 i.p. | 18.2 ± 1.7 | 9.2 ± 2.0 | 6.8 ± 1.1 | *2.1 ± 0.4 | 2.9 ± 0.9 |

*Significative difference p <0.05

From the above it can be seen that 2-(4-hydroxypyrrolidin-2-on-1-yl)-acetamide at a dose of 10 mg/kg per o.s. is as active as Piracetam at a dose of 30 mg/kg endoperitoneally while at the same dose endoperitoneally it displays an even higher activity than Piracetam at a dose of 30 mg/kg endoperitoneally. Further, the compounds produced by the invention do not display any hypotensive, tranquilizing, muscle relaxant or anti-convulsant activity. At a dose of 200 mg/kg (I.V. on anaesthetized cat) 2-(4-hydroxypyrrolidin-2-on-1-yl)-acetamide has no effect on arterial blood pressure and at the same does it has no effect on mono- and polysynaptic reflexes while at a dose of 500 mg/kg endoperitoneally it has no effect on the body tone and spontaneous motility (on mouse).

The compounds produced by the present invention improve learning memory and display a protecting effect against the E.E.G. consequence of an overdose of barbiturates and against the reduced performance following brain damage (e.e. cerebral edema).

What we claim is:

1. A process for the preparation of pyrrolidine compounds of the formula:

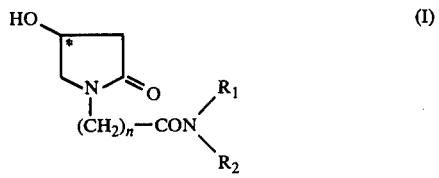

wherein $n$ is 1, 2 or 3, $R_1$ and $R_2$, which can be the same or different, are hydrogen or alkyl having 1 to 3 carbon atoms and the asterisk indicates the center of asymmetry of the molecule, either as separated enantiomers or as a mixture thereof, comprising (1) reacting γ-amino-β-hydroxybutyric acid, either as separated enantiometers or as a mixture, under anhydrous conditions with a silylating agent, (2) reacting the product obtained, in the presence of an acid acceptor, with a halogen compound of an ester of an aliphatic acid of the formula $Hal(CH_2)_n$—COOR, in which Hal is bromine, chlorine or iodine, R is alkyl having 1 to 4 carbon atoms, trichlorophenyl, nitrophenyl or trichloroethyl and $n$ has the same meaning as above, (3) cyclizing to give a silyl compound of the formula:

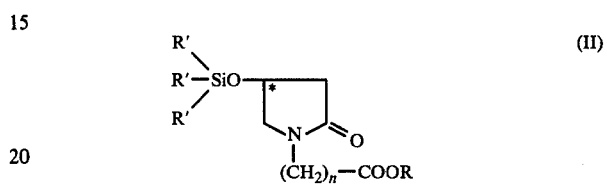

in which R' is methyl or ethyl and $n$, R and the asterisk have the same meanings as above, (4) hydrolyzing compound (II) to give the corresponding 4-hydroxy compound and (5) then reacting said 4-hydroxy compound with ammonia or with a mono- or disubstituted amine of the formula $R_1.NH.R_2$, in which $R_1$ and $R_2$ have the same meanings as above except that both cannot be hydrogen atoms.

2. A process according to claim 1, wherein the acid acceptor is a basic ion exchange resin, an olefin oxide, magnesium oxide or calcium oxide.

3. A process according to claim 1, wherein the silylating agent is hexamethyldisilazane, bis-(trimethylsilyl)-urea or bis-(trimethylsilyl)-acetamide.

4. A process according to claim 1, wherein the silylating agent is used in the presence of a small quantity of trimethylchlorosilane.

5. A process according to claim 1, wherein silylation is carried out in a low boiling, inert, aprotic solvent or in a mixture of low boiling, inert, aprotic solvents.

6. A process according to claim 5, wherein silylation is carried out in a mixture of acetonitrile with methylene chloride or chloroform.

7. A process according to claim 5, wherein silylation is carried out with the use of an excess of silylating agent at the boiling temperature of the solvent or solvent mixture used.

* * * * *

UNITED STATES PATENT OFFICE
CERTIFICATE OF CORRECTION

Patent No. 4,124,594     Dated November 7, 1978

Inventor(s) Riccardo Monguzzi, and Giorgio Pifferi

It is certified that error appears in the above-identified patent and that said Letters Patent are hereby corrected as shown below:

Abstract, line 3 from the bottom, change "barbituates" to --barbiturates--;

Column 1, line 42, change "inverted" to --converted--;

Column 5, line 28, change "e.e." to --e.g.--;

Column 5, line 20, change "does" to --dose--;

Column 6, line 6 from bottom, change "mixure" to --mixture--.

In Table and Table Continued:

Align "Dose mg/kg and route" with the column.

Signed and Sealed this

Twelfth Day of June 1979

[SEAL]

Attest:

RUTH C. MASON
Attesting Officer

DONALD W. BANNER
Commissioner of Patents and Trademarks